United States Patent [19]

Rebsdat et al.

[11] Patent Number: 4,471,071

[45] Date of Patent: Sep. 11, 1984

[54] SILVER CATALYSTS, AND A PROCESS FOR THEIR PREPARATION

[75] Inventors: Siegfried Rebsdat, Burg; Sigmund Mayer, Burgkirchen; Josef Alfranseder, Hofschallern, all of Fed. Rep. of Germany

[73] Assignee: Hoechst Aktiengesellschaft, Frankfurt am Main, Fed. Rep. of Germany

[21] Appl. No.: 500,262

[22] Filed: Jun. 2, 1983

[30] Foreign Application Priority Data

Jul. 24, 1982 [DE] Fed. Rep. of Germany ....... 3227753
Mar. 24, 1983 [DE] Fed. Rep. of Germany ....... 3310685

[51] Int. Cl.$^3$ ........................ B01J 23/04; B01J 23/50

[52] U.S. Cl. .................................. 502/347; 502/348; 549/534

[58] Field of Search ................. 502/347, 348; 549/534

[56] References Cited

U.S. PATENT DOCUMENTS

| | | | |
|---|---|---|---|
| 3,962,136 | 6/1976 | Nielsen et al. | 502/347 |
| 4,212,772 | 7/1980 | Mross et al. | 502/347 |
| 4,278,562 | 7/1981 | Mross et al. | 502/347 |

Primary Examiner—W. J. Shine

[57] ABSTRACT

A method for making a silver catalyst by applying a promoter and a complex formed between a silver salt and a mixture of a tert.-alkyl amine and a sec.-alkyl amine to a heat resistant porous support and then thermally decomposing said complex to metallic silver.

8 Claims, No Drawings

SILVER CATALYSTS, AND A PROCESS FOR THEIR PREPARATION

The invention relates to silver catalysts which consist of silver and a promoter on a heat-resistant porous support material. The invention also relates to a process for preparing these catalysts and to their use in the preparation of ethylene oxide by oxidizing ethylene with oxygen.

The large-scale production of ethylene oxide involves the direct oxidation of ethylene with oxygen on a silver catalyst. The process is described in general in Kirk-Othmer, Encyclopedia of Chemical Technology, volume 9, pages 432 to 471, John Wiley, London/New York, 1980.

An ethylene- and oxygen-containing gas enters the reactor at the top. The reactor consists of a bundle of several thousand tubes which are 6 to more than 10 m long. The gas flows over the catalyst present in the tubes, as a rule at a temperature of 150° to 400° C. under an overpressure of 0.15 to 3 MPa, and 5 to 20% of the starting ethylene reacts.

Not only is ethylene oxide formed, but a considerable proportion of the ethylene, namely about 25%, is oxidized to carbon dioxide and water (total oxidation), as the following equations are intended to show:

Ethylene oxide formation: $2C_2H_4 + O_2 \longrightarrow 2C_2H_4O$

Total oxidation: $C_2H_4 + 3O_2 \longrightarrow 2CO_2 + 2H_2O$.

For temperature control and heat dissipation, the tubes are surrounded by a heat transfer medium which carries the evolved heat out of the reactor. On leaving the reactor, the reaction gas, which contains ethylene oxide and carbon dioxide, passes into the working-up zone where the ethylene oxide and carbon dioxide are separated off. The gas, now freed from ethylene oxide and carbon dioxide, is again enriched with ethylene and oxygen and returned to the reactor. It is a continuous cycle process involving heterogeneous catalysis.

The catalyst used is a supported silver catalyst. The quality of such a catalyst is significantly determined by its selectivity, its activity and its life.

The selectivity is the molar percentage of converted ethylene which reacts to give ethylene oxide.

The activity is characterized by the ethylene oxide concentration at the reactor outlet under otherwise constant conditions (for example temperature, pressure, gas flow rate, amount of catalyst). The higher the ethylene oxide concentration, the higher is the activity. In other words: the lower the temperature required for a certain ethylene oxide concentration, the higher is the activity.

The preparation of supported silver catalysts per se has been known for a long time. They are preferably prepared by the following method:

The support material is soaked with a solution of a silver salt. The soaked support material is dried, the silver salt settling out on the support material. The support material thus impregnated with the silver salt is subjected to conditions under which the silver salt decomposes to form elemental silver which is present on the support in finely divided form. This step is carried out, for example, purely thermally by heating to about 170° to 400° C. or by means of such reducing agents as formaldehyde. The thermal reduction can be effected while inert gases, such as air, nitrogen, carbon dioxide or mixtures thereof, are passed over.

As a rule, the silver is applied to the support material together with promoters, such as potassium, rubidium and/or cesium, because they substantially improve the activity of the finished catalyst.

In recent years it has been found that highly active silver catalysts are obtained when the silver is applied by impregnating the support material with certain silver salt/amine complexes, for which a large number of proposals have been made since the original discovery.

In German Auslegeschrift No. 2,159,346, which corresponds to U.S. Pat. No. 3,702,259, the support material is impregnated with an aqueous solution which contains at least one silver carboxylate and, for forming a silver carboxylate/amine complex, at least one organic amine, this solubilizing/reducing organic amine being preferably ethylenediamine, a mixture of ethylenediamine and ethanolamine or of ammonia and ethylenediamine, or a mixture or ammonia and ethanolamine.

The silver catalyst disclosed in German Offenlegungsschrift No. 2,300,512 as consisting of silver in an amount of 3 to 20% by weight and potassium, rubidium and/or cesium or promoter in an amount of 0.003 to 0.05% by weight on a heat-resistant porous support material, all the weight percentages being relative to the weight of the catalyst, is likewise prepared by applying the silver to the support material in the form of a silver carboxylate/ethylenediamine and/or ethanolamine complex.

German Offenlegungsschrift No. 2,622,228 and German Auslegeschrift No. 2,640,540 mention, as complexing amines for the silver salt, which can be organic or inorganic, primary amines having alkyl radicals of 1 to 8 carbon atoms, polyamines of alkanes up to about hexane, alicyclic amines, such as cyclohexylamine, heterocyclic amines, such as pyrrolidone, piperidine or morpholine, and in particular amines of the general formula (R,R')-CH—NH$_2$, where R and R' are aliphatic radicals.

German Offenlegungsschriften Nos. 2,655,738 and 2,734,912 disclose that silver and the promoter cesium are deposited onto a support material by means of an impregnating solution which contains at least one silver carboxylate, at least one amine and at least one cesium compound soluble in the silver carboxylate/amine complex. The amines used are certain aliphatic diamines, aliphatic polyamines or certain aliphatic aminoethers. The impregnating solution can also contain water.

U.S. Pat. No. 4,235,757, finally, mentions amines of the formula NH$_2$—R—NH—R'—OH, in which R and R' are an alkyl group having 2 to 4 carbon atoms, as particularly advantageous complexing agents for applying silver to a support material.

The publications mentioned describe various ways of applying the silver and the promoter to the support material. For instance, in the processes of German Offenlegungsschriften Nos. 2,300,512 and 2,734,912 the silver (the silver salt/amine complex) and the promoter (the promoter compound) are applied at one and the same time to the support material, by means of impregnating. In the preparation of a silver catalyst in accordance with German Auslegeschrift No. 2,640,540, it is not critical how the silver and promoter are applied to the support. The silver and promoter can be applied at the same time and in one impregnating step or in succession, the promoter being deposited in a first and the silver in a second impregnating step or the silver being deposited in a first and the promoter in a second impregnating step.

The state of the art concerning the preparation of silver catalysts having improved properties by using silver salt/amine complexes thus already contains a large number of recommended complexing amines. There is, nevertheless, a need for further proposals in this direction, particularly since, on the one hand, existing amine complexing agents are frequently relatively difficult to prepare and, on the other, the improvement obtained with these agents in respect of activity, selectivity and life still leaves something to be desired.

We have now found, surprisingly, that a mixture of at least one tert.-alkylamine (tert. = tertiary) and at least one sec.-alkylamine (sec. = secondary) is particularly favorable for use as a complexing (solubilizing/reducing) amine, because it helps to give silver catalysts which not only have an unexpectedly high activity, selectivity and long life, but, surprisingly, show a dependence of selectivity on ethylene conversion which is so low as to be unobtainable with prior art amines. The action of the proposed amine (amine mixture) is independent of the manner in which silver and promoter are applied to the support.

In the silver catalyst of the invention, which consists of silver in an amount of 3 to 20% by weight and potassium, rubidium and/or cesium as promoter in an amount of 0.003 to 0.05% by weight on a heat-resistant porous support material, all the weight percentages being relative to the weight of the catalyst (weight of the finished catalyst or total weight of the catalyst), the silver and the promoter having been applied by impregnating the support material with silver salt/amine complexes and with promoter compounds and by drying and heating the impregnated support material to 170° to 400° C. to decompose the silver salt/amine complex into metallic silver, the amine used for forming the silver salt/amine complex is a mixture of (a) 10 to 40% by weight of at least one tert.-alkylamine of the general formula

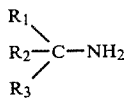

and (b) 60 to 90% by weight of at least one sec.-alkylamine of the general formula

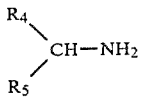

in which $R_1$, $R_2$, $R_3$, $R_4$ and $R_5$ denote an alkyl group having 1 to 4 carbon atoms.

The process of the invention, in which silver is applied to a heat-resistant porous support material in an amount of 3 to 20% by weight and potassium, rubidium and/or cesium as promoter in an amount of 0.003 to 0.05% by weight, all the weight percentages being relative to the weight of the catalyst (weight of the finished catalyst or total weight of the catalyst), the silver and the promoter being applied by impregnating the support material with silver salt/amine complexes and with promoter compounds and heating the impregnated support material to 170° to 400° C. to decompose the silver salt/amine complex into metallic silver, comprises using as amine to form the silver salt/amine complex a mixture of (a) 10 to 40% by weight of at least one tert.-alkylamine of the general formula

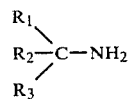

and (b) 60 to 90% by weight of at least one sec.-alkylamine of the general formula

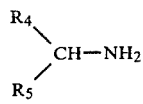

in which $R_1$, $R_2$, $R_3$, $R_4$ and $R_5$ denote an alkyl group having 1 to 4 carbon atoms.

The solubilizing/reducing amine mixture of the invention preferably comprises 20 to 30% by weight of at least one tert.-alkylamine and 70 to 80% by weight of at least one sec.-alkylamine.

Of the tert.-alkylamines and sec.-alkylamines which can be used in the invention, those which are preferred have methyl ($-CH_3$) or ethyl ($-C_2H_5$) as $R_1$ to $R_3$ or $R_4$ and $R_5$ alkyl groups. The particularly preferred tert.-alkylamine is tert.-butylamine, namely

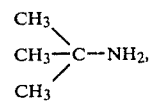

and the particularly preferred sec.-alkylamine is sec.-butylamine, namely

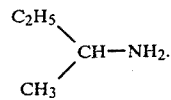

The complexing amine of the invention is used in at least the amount required for forming the silver salt/amine complex, i.e. the amount which completely dissolves the silver salt used. Since a silver cation of the reaction equation $Ag(amine)_2X$ (X = anion of the silver salt used) stoichiometrically binds two amino groups, it is necessary to use at least two amino groups per mole of silver cation. To ensure complete solubility, a small molar excess of the solubilizing amine is therefore generally used.

The amount of amine used in the invention is generally 2.05 to 5 moles, preferably 2.1 to 3 moles, of amine per mole of silver in the silver compound used.

In the novel silver catalyst, the amount of silver is preferably 7 to 14% by weight and the amount of promoter (potassium, rubidium or cesium or a mixture thereof) is preferably 0.08 to 0.035% by weight, the two weight percentages being relative to the weight of the catalyst.

The promoter is preferably cesium.

The type of silver salt and the type of promoter compound is in principle not critical for the impregnation of the support.

The silver salts used can be inorganic and/or organic salts. Advantageous organic salts are such silver carboxylates as silver formate, acetate, malonate, oxalate or lactate and/or silver citrate. Advantageous inorganic salts are silver carbonate, silver nitrate and/or silver nitrite. Of the silver salts mentioned, the preferred ones are silver acetate, silver lactate, silver oxalate, silver carbonate and/or silver nitrate; they are easily accessible and relatively inexpensive.

The promoter compounds used can be inorganic and/or organic compounds, salts and hydroxides being preferred. The anion of the promoter compound is not critical, since it is of no importance for catalytic activity; the promoter is active in the form of the cation in the promoter compound applied. Advantageous promoter salts are carboxylates, such as formate, acetate, malonate, oxalate, lactate, tartrate and/or citrate. Advantageous inorganic salts are carbonates, bicarbonates, phosphates, nitrates and/or nitrites. Of the promoter compounds mentioned, the preferred ones are the easily accessible and relatively inexpensive acetate and/or nitrate.

The customary, commercially available heat-resistant and porous materials are possible for use as support material for the silver catalysts of the invention. These materials are inert even under the reaction conditions prevailing in the oxidation of ethylene, and in the presence of the chemical compounds used. The support material for preparing the silver catalysts of the invention is not critical, examples of suitable supports being carbon, corundum, silicon carbide, silicon dioxide, aluminum oxide and mixtures of aluminum oxide and silicon dioxide. α-alumina is preferred, since it has a largely uniform pore diameter. It has a specific surface area of 0.1 to 1 $m^2/g$, preferably 0.2 to 0.6 $m^2/g$ (measured by the well-known B.E.T. method), a specific pore volume of 0.1 to 1 $cm^3/g$, preferably 0.2 to 0.6 $cm^3/g$ (measured by the well-known mercury or water adsorption method), an apparent porosity of 20 to 70% by volume, preferably 40 to 60% by volume (measured by the well-known mercury or water adsorption method), a mean pore diameter of 0.3 to 15 $\mu m$, preferably 1 to 10 $\mu m$, and a percentage of pores having a diameter of 0.03 to 10 $\mu m$ of at least 50% by weight (as is well-known, the pore diameter and pore diameter distribution are determined from the specific surface area and apparent porosity). The support material is advantageously used in the form of granules, spheres, rings, pellets or the like. Examples of preferred support materials made of α-alumina or containing α-alumina are the types sold by Norton Company, U.S.A., under the labels SA 5551 and SA 5552 and the SAHM types sold by United Catalyst, United States.

Silver and promoter are applied to the support material by means of the known impregnating method, in which the support material is brought into contact with the impregnating solution, preferably soaked therein (by dipping it into the solution or pouring the solution over it), and the solution penetrates into the pores of the support material, due to absorption and/or due to capillary action. Excess impregnating solution is then separated off (for example by pouring it off, allowing it to drip off, by filtering off the support material or by centrifuging) and as the fully saturated support material is being dried the silver compound and/or the promoter compound deposit onto it.

The amount of impregnating solution is generally chosen to be such that the volume of impregnating solution present is larger than the volume of support material to be impregnated. In general, the volume of impregnating liquid taken is 0.5 to 3 times, preferably equal to or twice, the volume of the support material. The impregnating time, i.e. the time during which the support material remains in contact with the impregnating liquid, should clearly be chosen in such a way that the required amount of silver compound and promoter compound to be deposited is applied to the support. The time generally amounts to 3 to 60 minutes and depends, in particular, on the concentration of silver compound and promoter compound in the impregnating solution, on the support material used and on its particular absorbence. The impregnating temperature used can vary within wide limits. Impregnating is generally carried out at room temperature. It is also possible to use elevated temperatures. The impregnating temperature accordingly is, as a rule, 15° to 80° C., preferably 20° to 50° C. Impregnating is generally carried out under atmospheric pressure. To accelerate the impregnating step, this can also be carried out in vacuo.

Suitable solvents for preparing the impregnating solutions are water, organic liquids and mixtures of water and organic liquids. Preferred solvents are water, methanol, ethanol, propanol, isopropanol and acetone as well as mixtures thereof.

The impregnated support material, once it has been freed from excess impregnating liquid, is generally dried at a temperature of 20° to 150° C., preferably 50° to 120° C. The solvent can be evaporated off by means of, for example, rack dryers, rotary tube dryers or the passage of hot inert gases, such as nitrogen, air and/or carbon dioxide. The temperature generally depends on the boiling point of the solvent of the impregnating liquid. In a preferred method, the drying is carried out at a temperature of 50° to 120° C. in the presence of inert gas.

The silver salt/amine complex deposited in the dried impregnated support material is converted (reduced or thermally decomposed) into metallic silver by heating the support material to a temperature of 170° to 400° C. in general, preferably to a temperature of 200° to 350° C. The heating to these temperatures can be carried out in, for example, a rack dryer, a rotary tube dryer or an electrically heated tube or by passing over a suitably hot inert gas, such as air, nitrogen, carbon dioxide or a mixture thereof. The silver/amine complex can also be converted into metallic silver by means of superheated steam. In a preferred method, the silver compound applied to the support material is thermally decomposed by passing air, nitrogen and/or carbon dioxide over the hot fully impregnated support material (precatalyst) at 200° to 350° C. The heating time for the temperatures mentioned is generally 0.05 to 5 hours, preferably 0.1 to 1 hour. As the silver compound decomposes, a firmly adhering deposit of metallic silver particles forms on the support material (the promoter compounds are not reduced to the corresponding metal; the alkali metals potassium, rubidium and cesium are thus essentially present in the form of their cations and not as free alkali metals). The silver (the silver particles) is generally present in the form of firmly adhering discrete particles which are essentially uniformly distributed and do not hang together.

The way the silver content (in the form of the silver salt/amine complex starting material) and the promoter content (in the form of the promoter compound starting material) are applied as part of the impregnating process is not critical. Silver and promoter can thus be applied to the support at the same time or at different times, i.e. one after the other in any order. If silver and promoter are deposited at the same time, the total amount of silver and promoter can be applied in one impregnating step. It is also possible to use several impregnating steps, preferably two, only part of the total amount of silver and promoter being applied in each impregnating step. In this case, it has proved advantageous to apply to the support 55 to 85% by weight of the total amount of silver in a first impregnating step and, at the same time, 15 to 45% by weight of the total amount of promoter, followed, after drying, by a second impregnating step for the respective remainders. If the silver and promoter are deposited in succession, the silver can be applied first, followed by the promoter, or the promoter can be applied first, followed by the silver, in each case in one or more impregnating steps. If the silver compound is applied first, followed by the promoter compound, the silver compound can be reduced to metallic silver before the promoter compound is applied, but it is also possible to carry out only an intermediate drying step. In a further method, the total amount of silver and only part of the total amount of promoter are applied in one impregnating step, followed in a second impregnating step by the remaining amount of promoter. In this case it proved advantageous to deposit the total amount of silver and 15 to 45% by weight of the total amount of promoter in the first impregnating step, to reduce the silver compound to metallic silver, and to deposit the remainder of the total amount of promoter in a second impregnating step. By analogy, the total amount of promoter and only part of the total amount of silver can be applied in a first impregnating step, followed in a second impregnating step by the remaining amount of silver. It is also possible to proceed by, for example, alternately applying the silver and promoter to the support in the course of several impregnating steps. For example, first some of the total amount of silver is deposited, then, in one or more impregnating steps, the amount of promoter, followed, at the end, by the remaining amount of silver. By analogy, it is also possible to start with the promoter.

The impregnating solutions for the chosen impregnating method can vary within wide limits in respect of the concentration of silver compound and promoter compound. These concentrations are known to be determined by the desired silver and promoter contents of the support in particular. The concentration of silver and promoter in the impregnating solutions merely has to be chosen in such a way that 3 to 20% by weight, preferably 7 to 14% by weight, of silver and 0.003 to 0.05% by weight, preferably 0.008 to 0.035% by weight, of promoter are deposited in the course of the impregnating. The appropriate concentration can be easily and rapidly determined in preliminary experiments and by analytical measurement of the amount of silver compound and promoter compound deposited on the support. An impregnating solution appropriate for the simultaneous application of silver and promoter to the support by means of one or more impregnating steps, for example, essentially consists of (a) water, (b) 30 to 40% by weight of silver compound, (c) 2.1 to 3 moles of amine of the novel amine mixture per mole of silver in the silver compound starting material and (d) 0.03 to 0.1% by weight of promoter compound, all the weight percentages being relative to the weight of the solution. Examples of solutions suitable for applying silver and for applying the promoter in one or more impregnating steps in each case are (a) water, (b) 30 to 40% by weight of silver compound and (c) 2.1 to 3 moles of amine of the novel amine mixture per mole of silver in the silver compound starting material, or (a) water or a mixture of water and an organic solvent, preferably methanol, ethanol, propanol, isopropanol or acetone, and (b) 0.03 to 0.1% by weight of promoter compound, all the weight percentages being relative to the weight of the solution (where, in these impregnating solutions, the solvent is thus present in such an amount that it makes up to 100% by weight the specified amount of the other components).

The silver catalyst of the invention has a high activity and selectivity and a long life. It is particularly distinguished by the surprisingly low dependence of the selectivity on the ethylene conversion.

The ethylene oxide formation selectivity of a silver catalyst is known to depend on the amount of ethylene converted in the reactor, in such a way that an increase in ethylene conversion leads to a decrease in selectivity. This degree of dependence varies from silver catalyst to silver catalyst, and constitutes a considerable disadvantage, because, in the economically motivated desire to operate ethylene oxide plant at increasingly high utilization, i.e. at an increasingly high ethylene conversion, the decreasing selectivity and hence increasing ethylene losses must necessarily be accepted. The lower the drop in selectivity as ethylene conversion increases, accordingly the better is a silver catalyst.

The selectivity of the silver catalyst of the invention is much less dependent on ethylene conversion than prior art silver catalysts. An associated great advantage is that the amount of catalyst required can be kept relatively small, compared with existing silver catalysts. In view of the high price of silver catalysts, this clearly is a considerable economic benefit. Furthermore, the gas flow rate used in conjunction with the silver catalyst of the invention can be relatively small, so that there is a saving in energy in connection with the compression of the gas.

On using the silver catalyst of the invention, a good selectivity is thus obtained with a relatively low gas flow rate and a relatively high ethylene conversion, on top of which there are all the other abovementioned advantages.

The process of the invention for preparing the new silver catalysts is simple and easy to carry out. It contains no complicated or elaborate steps. Nor does it require special impregnating solutions. The amines to be used in the invention are easily accessible, easy to handle and inexpensive.

The new silver catalyst is used under conditions known per se, such as temperature, pressure, residence time, diluents, moderators for controlling the catalytic oxidation of ethylene with oxygen, recycling, process-related measures for increasing the ethylene oxide yield, and the like. The reaction temperature is generally 150° to 400° C., preferably 175° to 250° C., and the reaction pressure is 0.15 to 3 MPa, preferably 1 to 2 MPa. The feed mixture generally contains 5 to 30 mole % of ethylene, 3 to 15 mole % of oxygen and, as a remainder, inert gases, such as nitrogen, carbon dioxide, steam, methane, ethane, argon or the like, and vinyl chloride, 1,2-dichloroethane and the like as moderators. The ethylene oxide is isolated in a conventional manner from the reaction product, and the gas mixture is conventionally purified, if desired, and returned. In a preferred embodiment of the use of the silver catalysts of the invention, ethylene oxide is prepared by oxidizing ethylene at a temperature of 175° to 250° C. in the presence of the new silver catalyst with a gas mixture containing about 8.5% by weight of oxygen.

The invention will now be illustrated in more detail by means of Examples.

EXAMPLE 1

To prepare a catalyst of the invention, a solution was prepared from

| | | |
|---|---|---|
| 21.000 g | (26.5655% by weight) | of water |
| 30.000 g | (37.9502% by weight; 0.177 mole of silver) | of silver nitrate |
| 7.000 g | (8.8555% by weight; 0.096 mole) | of tert.-butylamine |
| 21.000 g | (26.5655% by weight; 0.287 mole) | of sec.-butylamine |
| 0,050 g | (0.0633% by weight) | of cesium nitrate |

(0.383 mole of amine of the invention was thus used in the form of 25% by weight of tert.-butylamine and 75% by weight of sec.-butylamine per 0.177 mole of silver, i.e. 2.16 moles of this amine per mole of silver).

The SAHM support material from United Catalyst, namely α-alumina in the form of cylinders having a specific surface area of 0.2 m²/g, was completely dipped at 40° C. for 15 minutes into this solution. When excess impregnating solution had dripped off, the moist support material was dried at 110° C. for 30 minutes in an air/nitrogen atmosphere.

25 g of the support thus soaked and dried were then packed into a preheated glass tube at 200° C. to reduce the silver compound present on the support. 30 liters of air per hour were allowed to flow upwards through the tube, which had an internal diameter of 30 mm and a length of 300 mm. Nitrogen was blown in at a rate of 60 liters per hour at a point about 50 mm above the support to be reduced, to prevent a possible explosion. Reduction for half an hour gave the finished, ready-for-use silver catalyst, which contained 8.7% by weight of silver and 0.014% by weight of cesium.

20 ml of this catalyst were reacted at 185° C. in a glass reactor under atmospheric pressure with an ethylene/oxygen mixture. This mixture contained 30% by volume of ethylene, 8% by volume of oxygen and 0.0003% by volume of vinyl chloride, the rest being nitrogen. The catalyst was subjected to a weight hourly space velocity of 400 liters of gas per liter of catalyst per hour.

The reaction product leaving the reactor contained 1.8% by volume of ethylene oxide. The selectivity (number of moles of ethylene oxide formed per mole of ethylene reacted) and the ethylene conversion (% by volume of converted ethylene, relative to starting ethylene) were calculated from an analysis of the resulting ethylene oxide and carbon dioxide and the amount of converted ethylene. The results were a selectivity of 80.7% and an ethylene conversion of 7.7%.

The selectivity was not found to decrease even in the course of a 2 month experimental period.

The reaction temperatures were raised from 185° C. to 192° C. to examine the dependence of this catalyst's selectivity on ethylene conversion. The ethylene conversion was now 12% (formerly 7.7%) and the amount of ethylene oxide formed 2.9% by volume (formerly 1.8% by volume). The selectivity was found to be 79.0%. In other words, as the ethylene conversion increased by 4.3% points the selectivity decreased by only 1.7% points.

EXAMPLE 2

To prepare the catalyst of the invention, a solution was prepared from

| | | |
|---|---|---|
| 21.000 g | (26.9058% by weight) | of water |
| 30.000 g | (38.4369% by weight; 0.179 mole of silver) | of silver acetate |
| 5.000 g | (6.4061% by weight; 0.068 mole) | of tert.-butylamine |
| 22.000 g | (28.1871% by weight; 0.301 mole) | of sec.-butylamine |
| 0.050 g | (0.0641% by weight) | of cesium acetate |

(0.369 mole of amine of the invention was thus used in the form of 18.5% by weight of tert.-butylamine and 81.5% by weight of sec.-butylamine per 0.179 mole of silver, i.e. 2.06 moles of this amine per mole of silver).

The support material used was SA 5552 from Norton, an α-alumina in the form of cylinders having a specific surface area of 0.3 m²/g. The support material was impregnated at 50° C. for 15 minutes, and then dried and reduced as in Example 1. This gave a silver catalyst containing 8.8% by weight of silver and 0.015% by weight of cesium.

Under the test conditions of Example 1 at 183° C., this catalyst produced 1.8% by volume of ethylene oxide. A selectivity of 80.5% and an ethylene conversion of 7.9% were calculated from the analytically determined amounts of ethylene oxide, carbon dioxide and converted ethylene. On raising the temperature to 190° C., the catalyst produced 2.8% by volume of ethylene oxide with a selectivity of 79% at an 11.7% ethylene conversion. In other words, as the ethylene conversion increased by 3.8% points the selectivity decreased by only 1.5% points.

No decrease in selectivity was observed even after a 2 months experimental period under these conditions.

EXAMPLE 3 (COMPARATIVE EXAMPLE)

This example, unlike the examples of the invention, was carried out without tert.-butylamine. Example 2 was repeated. The impregnating solution consisted of

| | | |
|---|---|---|
| 21.000 g | (26.5655% by weight) | of water |
| 30.000 g | (37.9505% by weight; 0.177 mole of silver) | of silver nitrate |
| 28.000 g | (35.4207% by weight; 0.383 mole) | of sec.-butylamine |
| 0.050 g | (0.0633% by weight) | of cesium acetate |

The resulting silver catalyst contained 8.6% by weight of silver and 0.015% by weight of cesium.

Under the test conditions of Example 1 at 193° C., this catalyst produced 1.8% by volume of ethylene oxide. A selectivity of 79.5% and an ethylene conversion of 8% were calculated. On raising the reaction temperature to 195° C., 2.7% by volume of ethylene oxide were produced, and the selectivity was found to be 77% and the ethylene conversion 12%. An increase in ethylene conversion by 4% points lowered the selectivity by 2.5% points. The selectivity decreased by a further 0.3% point in the course of a 2 month experimental period under these conditions.

EXAMPLE 4 (COMPARATIVE EXAMPLE)

Example 2 was repeated, except that a mixture of 5.0 g of ethanolamine and 12.0 g of ethylenediamine, as in German Pat. No. 2,159,346 (equivalent to U.S. Pat. No. 3,702,259), was used in place of the amine mixture of the invention. The impregnating solution consisted of

| | |
|---|---|
| 21.000 g (30.8597% by weight) | of water |
| 30.000 g (44.0852% by weight; 0.179 mole of silver) | of silver acetate |
| 5.000 g (7.3475% by weight; 0.082 mole) | of ethanolamine |
| 12.000 g (17.6341% by weight; 0.200 mole) | of ethylenediamine |
| 0.050 g (0.0735% by weight) | of cesium acetate |

(The 0.082 mole of ethanolamine corresponds to 0.46 mole of ethanolamine per mole of silver, and the 0.200 mole of ethylenediamine corresponds to 1.12 moles of ethylenediamine per mole of silver; ethylenediamine contains two amino groups.)

This catalyst was tested as in Example 1. The result of the test is shown below.

| Temperature °C. | Ethylene conversion % | Selectivity % |
|---|---|---|
| 192 | 7 | 78.5 |
| 196 | 11 | 75.5 |

EXAMPLE 5 (COMPARATIVE EXAMPLE)

Example 2 was repeated, except that 30.0 g of the amine $H_2N-CH_2CH_2-NH-CH_2CH_2-OH$, as in U.S. Pat. No. 4,235,757, were used in place of the amine mixture of the invention. The impregnating solution consisted of

| | |
|---|---|
| 21.000 g (25.9099% by weight) | of water |
| 30.000 g (37.0142% by weight; 0.179 mole of silver) | of silver acetate |
| 30.000 g (37.0142% by weight; 0.289 mole) | of $H_2N-CH_2CH_2-NH-CH_2CH_2-OH$ |
| 0.050 g (0.0617% by weight) | of cesium acetate |

(The 0.289 mole of the amine corresponds to 1.61 moles of amine per mole of silver; this amine contains two complexing amino groups.)

This catalyst was tested as in Example 1. The result of the test is shown below.

| Temperature °C. | Ethylene conversion % | Selectivity % |
|---|---|---|
| 192 | 7 | 79 |
| 196 | 10 | 76.5 |

EXAMPLE 6

To prepare a catalyst of the invention, 91.5 g of alumina rings were dipped at 40° C. for 5 minutes, in the manner described in Example 1, into a solution of

| | |
|---|---|
| 10.500 g (26.5823% by weight) | of water |
| 15.000 g (37.9747% by weight; 0.088 mole of silver) | of silver nitrate |
| 3.800 g (9.6203% by weight; 0.052 mole) | of tert.-butylamine |
| 10.200 g (25.8227% by weight; 0.0139 mole) | of sec.-butylamine |

(0.0191 mole of amine of the invention was thus used in the form of 27% by weight of tert.-butylamine and 73% by weight of sec.-butylamine per 0.088 mole of silver, i.e. 2.16 moles of this amine per mole of silver). When excess impregnating solution had dripped off, the support material was dried at 110° C. for 30 minutes. The support thus soaked and dried was then dipped at 40° C. for three minutes into a solution of 0.670 g (0.0670% by weight) of cesium nitrate
994.330 g (99.4330% by weight) of methanol
5.000 g (0.500% by weight) of water and, when excess solution had dripped off, was dried at 110° C. for 15 minutes. The reduction was carried out as described in Example 1.

The finished catalyst, which had been prepared by applying to the support first the entire amount of silver (first impregnating step) and then (second impregnating step) the entire amount of cesium, contained 8.7% by weight of silver and 0.017% by weight of cesium.

Under the test conditions of Example 1 at 189° C., the catalyst produced 1.5% by volume of ethylene oxide, performing with a selectivity of 81% at an ethylene conversion of 7%.

EXAMPLE 7

To prepare a catalyst of the invention, 91.5 g of alumina rings were dipped at room temperature for 5 minutes, in the manner described in Example 1, into a solution of 0.900 g (0.090% by weight) of cesium nitrate
999.100 g (99.910% by weight) of water.
Excess solution was decanted off, and the support was dried at 110° C. for 1 hour.

When the rings had cooled down to room temperature, they were placed in an agitated drum, doused with 36 g of a silver impregnating solution prepared from

| | |
|---|---|
| 10.500 g (26.5823% by weight) | of water |
| 15.000 g (37.9747% by weight; 0.088 mole of silver) | of silver nitrate |
| 3.500 g (8,8607% by weight; 0.048 mole) | of tert.-butylamine |
| 10.500 g (26.5823% by weight; 0.144 mole) | of sec.-butylamine | and stirred at room temperature for 3 minutes (0.192 mole of amine of the invention was thus used in the form of 25% by weight of tert.-butylamine and 75% by weight of sec.-butylamine per 0.088 mole of silver, i.e. for 2.16 moles of this amine per mole of silver).

The drum contents were left to stand for 5 minutes, were dried at 110° C. for 30 minutes, and were then reduced in an air/nitrogen stream in the manner described in Example 1.

The finished catalyst, which had been prepared by applying to the support first the entire amount of cesium (first impregnating step) and then (second impregnating step) the entire amount of silver, contained 8.6% by weight of silver and 0.018% by weight of cesium.

Under the test conditions of Example 1 at 190° C., this catalyst produced 1.6% by volume of ethylene oxide, performing with a selectivity of 80.8% at an ethylene conversion of 6%.

EXAMPLE 8

To prepare a catalyst of the invention, first a solution was prepared from

| | | |
|---|---|---|
| 26.582 g | (26.5823% by weight) | of water |
| 37.975 g | (37.9747% by weight; 0.223 mole) | of silver nitrate |
| 8.860 g | (8.8607% by weight; 0.121 mole) | of tert.-butylamine |
| 26.590 g | (26.5823% by weight; 0.363 mole) | of sec.-butylamine |

(0.484 mole of amine of the invention was used in the form of 25% by weight of tert.-butylamine and 75% by weight of sec.-butylamine per 0.223 mole of silver, i.e. 2.17 moles of this amine per mole of silver).

90 g of the support material of Example 1 were doused in a rotary plastic drum in a first impregnating step with 35.2 g of the silver/amine impregnating solution specified above. The support material absorbed the entire solution. The drum contents were then dried in a drying cabinet at 120° C. for 40 minutes (the weight loss amounted to 10 g). In the course of this treatment, 25.8 g of a silver salt/amine complex, which corresponds to 8.5 g of silver, were applied to the support. Where they had cooled down to room temperature, the rings, in the agitated drum described above, were subjected to a second impregnating step, in which they were sprayed with a cesium impregnating solution of 38 mg of cesium nitrate in 10 g of water, the entire solution being sprayed on. The rings were then dried at 120° C. (the weight loss amounted to 9 g). In the course of this second impregnating step, the entire amount of cesium was applied. When the rings had cooled down to room temperature, they were impregnated for a third time— this time with 8.6 g of the abovementioned silver/amine impregnating solution, applied in the same way as in the first impregnating step—and were then dried at 110° C. for 30 minutes.

The unfinished catalyst thus prepared was reduced by means of an air/nitrogen mixture in the manner described in Example 1. The finished catalyst contained 10.6% by weight of silver and 0.026% by weight of cesium.

The catalyst was tested as in Example 1, with the following result:

| Temperature (°C.) | Ethylene conversion (% by volume) | Selectivity (%) |
|---|---|---|
| 193 | 7 | 81.3 |
| 197 | 10 | 79.5 |

EXAMPLE 9

Example 8 was repeated, except that the sequence of impregnating steps was changed as follows:
1st impregnating step: first application of silver;
2nd impregnating step: second application of silver;
3rd impregnating step: application of cesium.

The finished catalyst contained 10.6% by weight of silver and 0.026% by weight of cesium.

The catalyst was tested as in Example 1, with the following result:

| Temperature (°C.) | Ethylene conversion (% by volume) | Selectivity (%) |
|---|---|---|
| 194 | 7 | 81.1 |
| 198 | 10 | 79.2 |

We claim:

1. A method for making a silver catalyst consisting of a heat resistant porous support material having thereon from 3 to 20 percent of silver and from 0.003 to 0.05 percent of a promoter which is a compound of potassium, rubidium, cesium, or a mixture thereof, said percentages being by weight of the finished catalyst, which method comprises impregnating said support material with said promoter compound and with a complex formed between a silver salt and an amine mixture comprising from 10 to 40 percent by weight of at least one tert.-alkyl amine of the formula

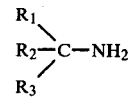

and from 60 to 90 percent by weight of at least one sec.-alkyl amine of the formula

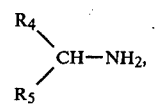

wherein $R_1$, $R_2$, $R_3$, $R_4$, and $R_5$ are each alkyl having 1 to 4 carbon atoms, and then drying and heating the impregnated support material at a temperature from 70° C. to 400° C. to decompose said complex into metallic silver.

2. A method as in claim 1 wherein said amine mixture comprises tert.-butylamine and sec.-butylamine.

3. A method as in claim 1 wherein said catalyst contains from 7 to 14 percent by weight of silver and from 0.008 to 0.035 percent by weight of said promoter.

4. A method as in claim 1 wherein said promoter is cesium.

5. A silver catalyst prepared by the method of claim 1.

6. A silver catalyst prepared by the method of claim 2.

7. A silver catalyst prepared by the method of claim 3.

8. A silver catalyst prepared by the method of claim 4.

* * * * *